US006800756B2

(12) United States Patent
Deshpande et al.

(10) Patent No.: US 6,800,756 B2
(45) Date of Patent: Oct. 5, 2004

(54) METHOD FOR THE PREPARATION OF CEFTIOFUR SODIUM AND ITS INTERMEDIATES

(75) Inventors: Pandurang Balwant Deshpande, Chennai (IN); Praven Kumar Luthra, Chennai (IN); Pratik Ramesh Sathe, Chennai (IN); Sivakumaran Sundaravadivelan, Chengalpattu (IN); Praveen Nagesh Ganesh, Chennai (IN)

(73) Assignee: Orchid Chemicals and Pharmaceuticals, Ltd., Tamilnadu (IN)

( * ) Notice: Subject to any disclaimer, the term of this patent is extended or adjusted under 35 U.S.C. 154(b) by 106 days.

(21) Appl. No.: 10/207,103

(22) Filed: Jul. 30, 2002

(65) Prior Publication Data

US 2003/0216567 A1 Nov. 20, 2003

(30) Foreign Application Priority Data

May 3, 2002 (IN) .................................... 338/MAS/2002

(51) Int. Cl.[7] .......................................... C07D 501/36
(52) U.S. Cl. ...................................... 540/226; 540/227
(58) Field of Search ................................. 540/226, 227

(56) References Cited

U.S. PATENT DOCUMENTS

| 4,464,367 | A | | 8/1984 | Labeeuw et al. | |
|---|---|---|---|---|---|
| 4,877,782 | A | | 10/1989 | Cazers et al. | |
| 4,902,683 | A | | 2/1990 | Amin et al. | |
| 6,384,215 | B1 | * | 5/2002 | Deshpande et al. | 540/227 |
| 6,388,070 | B1 | * | 5/2002 | Deshpande et al. | 540/227 |
| 6,458,949 | B1 | * | 10/2002 | Handa et al. | 540/226 |
| 6,552,186 | B2 | * | 4/2003 | Gerlach et al. | 540/227 |

FOREIGN PATENT DOCUMENTS

| CA | A 1146 165 | 5/1983 |
|---|---|---|
| EP | 0 842 937 A2 | 5/1998 |

OTHER PUBLICATIONS

Greene, "Protecting Groups in Organic Synthesis" (Wiley & Sons) 1981) page 177.*

* cited by examiner

Primary Examiner—Mark L. Berch
(74) Attorney, Agent, or Firm—Oliff & Berridge, PLC

(57) ABSTRACT

The present invention relates to preparation of Ceftiofur acid of formula (I),

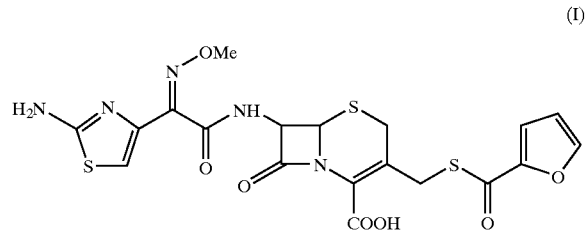

and its pharmaceutically acceptable salts. The process includes the steps of (i) condensing an activated derivative of

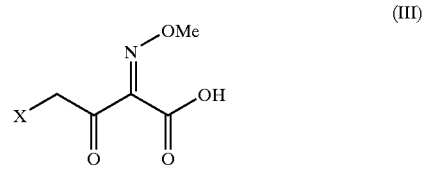

wherein the activated derivative is selected from acid halides, mixed anhydrides and active amides, and wherein X represents halogen atom selected from chlorine and bromine, with silylated derivative of

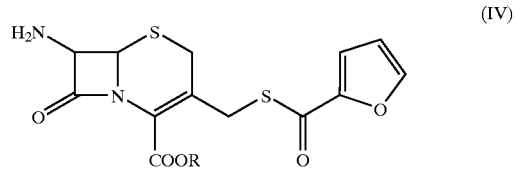

wherein R represents p-methoxybenzyl, p-nitrobenzyl or diphenylmethyl in the presence of a solvent at −40° C. to 0° C. to produce

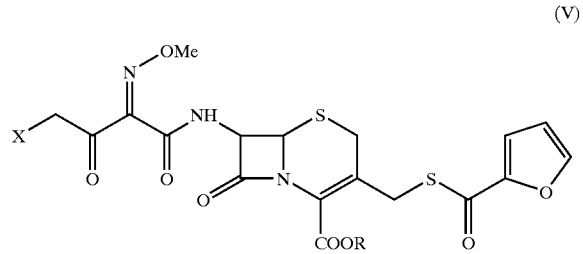

(ii) cyclising (V) with thiourea in the presence of water miscible solvent and sodium acetate at room temperature to produce cephalosporin

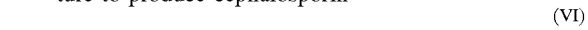
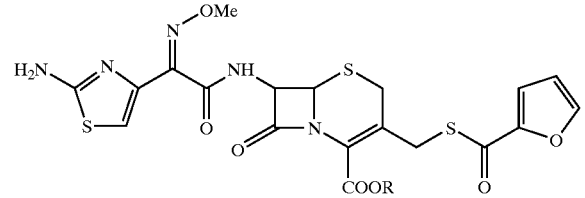

(iii) deesterifying (VI) to produce (I) using anisole/trifluoroacetic acid, phenol/trifluoroacetic acid or formic acid at 0° C. to 10° C. and, if desired,
(iv) converting (I), to its pharmaceutically acceptable salt. The invention also relates to intermediates (V) and (VI)
(V)
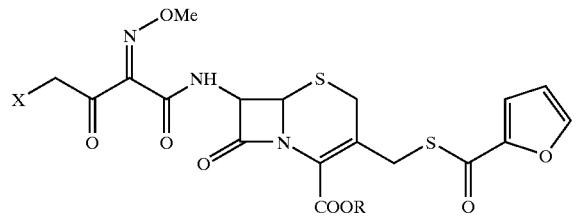
-continued
(VI)
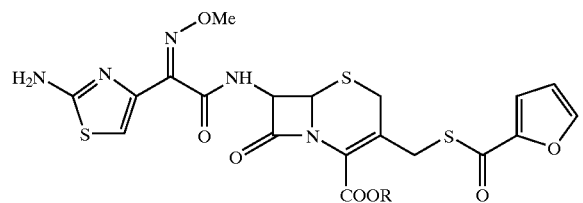
8 Claims, No Drawings

METHOD FOR THE PREPARATION OF CEFTIOFUR SODIUM AND ITS INTERMEDIATES

FIELD OF INVENTION

The present invention relates to a new method for the preparation of Ceftiofur acid of formula (I):

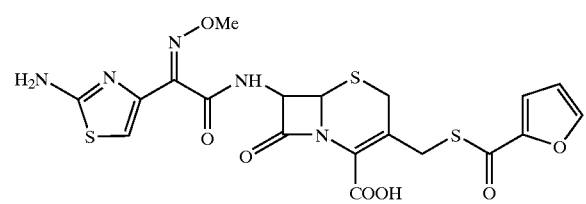

(I)

and its pharmaceutically acceptable salt such as sodium or hydrochloride.

The present invention also provides two new intermediates of formulae (V) and (VI):

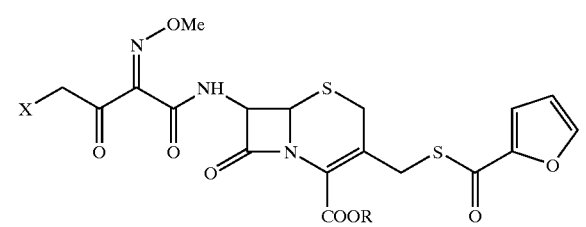

(V)

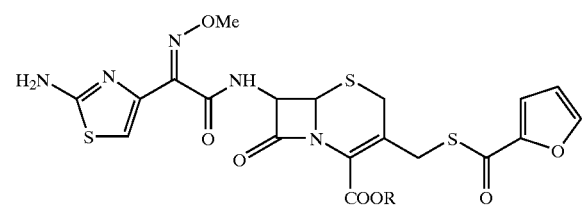

(VI)

wherein X represents halogen atom such as chlorine or bromine, R represents p-methoxybenzyl, p-nitrobenzyl or diphenylmethyl group.

BACKGROUND OF THE INVENTION

Ceftiofur acid, its alkali metal, alkaline earth metal and amines salts were reported for the first time in U.S. Pat. No. 4,464,367. During the course of further investigation, later on, it was discovered that all these derivatives of Ceftiofur are known to have stability problems. Further, it was difficult to purify the derivative of Ceftiofur due to amorphous nature of the compound. In fact, from the beginning, preparation of Ceftiofur sodium has posed challenges to organic chemists regarding purity, stability and crystallinity.

Several attempts have been made to prepare Ceftiofur sodium for obviating above-mentioned problems. One of the solutions was provided in U.S. Pat. No. 4,877,782 by preparing zinc complexes of Ceftiofur which have better dispersibility in water and can be used in pharmacological preparations. U.S. Pat. No. 4,902,683 also explains the isolation of more stable Ceftiofur in the form of crystalline hydrohalide salts which has better solubility and other physical properties, as compared to parent compounds. During the isolation of Ceftiofur hydrochloride salt most of the impurities present in the compound are removed during filtration. The hydrohalide salts as such cannot be used for parenteral administration, therefore it is necessary to convert a hydrohalide salt to sodium salt in order to use the drug as injectable.

EP 0030294 discloses the condensation of the 4-halogeno-2-substitutedimino-3-oxo-butyric acid with cephem carboxylic acids by using $PCl_5$ Another EP patent 0 842 937 discloses the formation of amide bond with cephem moiety by reacting with the thioester derivative of 4-chloro-2-methoxyimino-3-oxo-butyric acid. The thioester was prepared by reacting 4-chloro-2-methoxyimino-3-oxo-butyric acid with 2,2'-dithio-bis-benzothiazole in the presence of triphenyl phosphine which is costly material and its by product triphenyl phosphine oxide is also difficult to remove from the reaction mixture.

OBJECTIVES OF THE INVENTION

The primary objective of the invention is to provide a new method for the preparation of Ceftiofur acid of formula (I), which would be easy to implement in commercial scales.

Another objective of the present invention is to provide the novel intermediates of formulae (V) and (VI), which are useful in the preparation of Ceftiofur derivatives.

Another objective of the present invention is to provide a process for the preparation of intermediates of the general formulae (V) and (VI), in good yields with high purity.

SUMMARY OF THE INVENTION

In accordance, the present invention provides a new method for the preparation of ceftiofur acid of formula (I) and its pharmaceutically acceptable salt such as sodium or hydrochloride and also provides two intermediates of formulae (V) and (VI).

DETAILED DESCRIPTION OF THE INVENTION

Accordingly, the present invention provides a method for the preparation of Ceftiofur acid of formula (I):

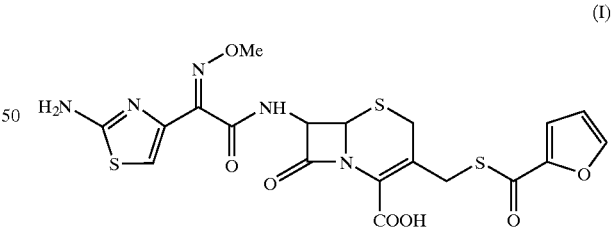

(I)

and its pharmaceutically acceptable salt such as sodium or hydrochloride, which comprises the steps of:

(i) condensing an activated derivative of formula (III) where X represents halogen atom such as chlorine or bromine, with silylated derivative of 7-amino cephalosporin of formula (IV) wherein R is as defined earlier in the presence of a solvent at a temperature in the range of −40° C. to 0° C. to produce a compound of formula (V), where R is as defined earlier, (ii) cyclising the compound of formula (V) with thiourea in the presence of water miscible solvent and sodium acetate at room temperature to produce cephalosporin compounds of formula (VI) wherein R is as defined earlier, (iii) deesterifying the compound of formula (VI) using anisole/trifluroacetic acid, phenol/trifluroacetic acid or formic acid in the presence or absence of a solvent at a temperature in the range of 0° C. to 10° C. to produce a compound of formula (I) and, if desired, (iv) converting the compound of formula (I) to its pharmaceutically acceptable salt.

The process is as shown in Scheme-1 below:

wherein R represents p-methoxybenzyl, p-nitrobenzyl or diphenylmethyl group.

In still another embodiment of the present invention the compound of formula (IV) can be prepared by a process which comprises protecting the compound of formula (VII) using p-methoxybenzyl halide, p-nitrobenzyl halide, or diphenylmethane halide or diphenyldiazomethane, in the presence of a solvent and base.

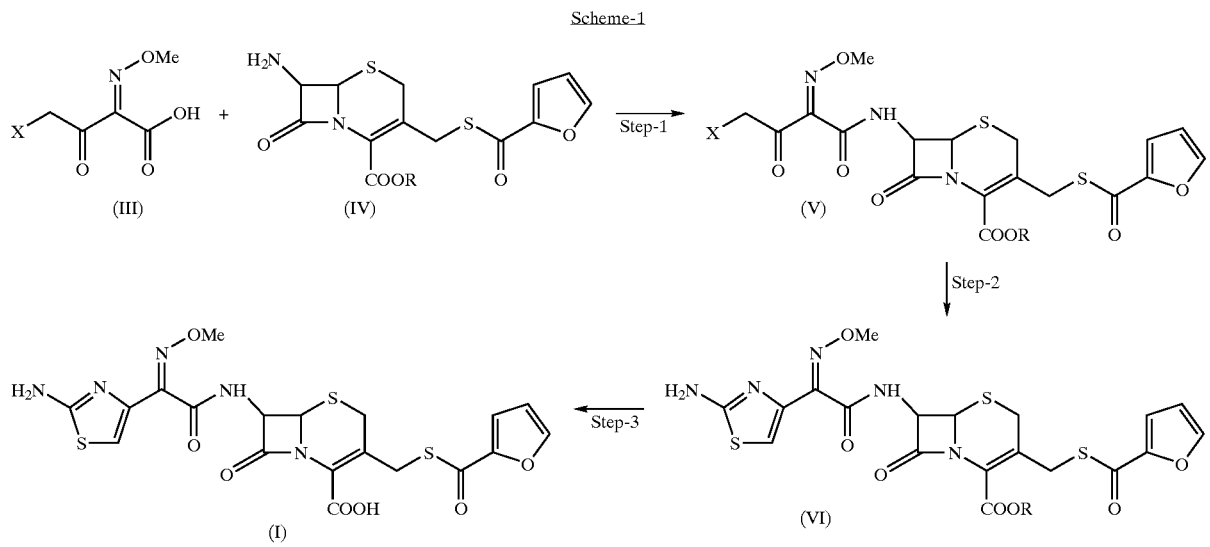

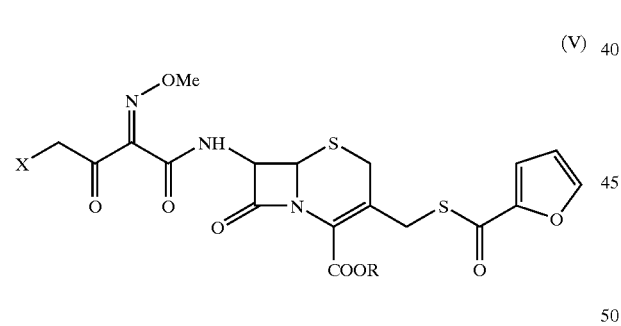

In another embodiment of the present invention, there is provided a new intermediate of formula (V):

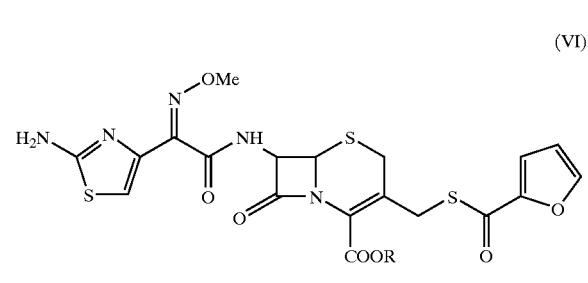

wherein X represents halogen atom such as chlorine or bromine, R represents p-methoxybenzyl, p-nitrobenzyl or diphenylmethyl group.

In yet another embodiment of the present invention, there is provided a new intermediate of formula (VI):

The process is as shown in Scheme-2 below

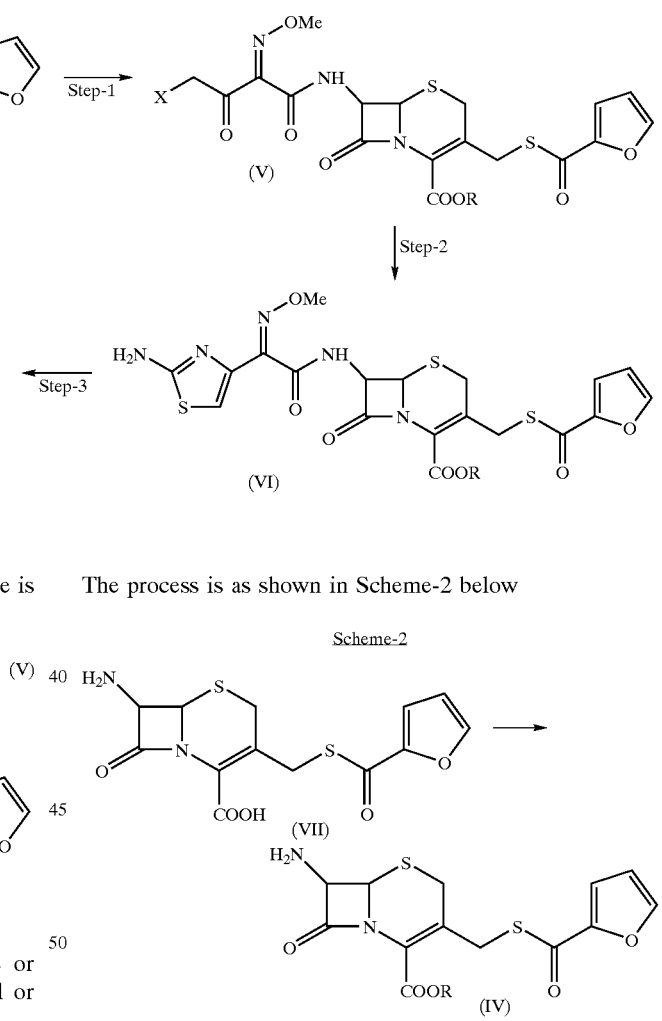

In still another embodiment of the present invention, there is provided an alternate process for the preparation of a compound of formula (IV), which comprises:

(i) condensing the 7-aminocephalosporin derivative of formula (VIII) wherein $R_1$ represents hydrogen, $(C_1–C_4)$alkyl, substituted or unsubstituted phenyl or substituted or unsubstituted phenoxy with furyl-2-carbonylthiol of formula (IX) in the presence in an organic solvent and a base at a temperature in the range of 0° C. to 30° C. to produce 7-aminocephalosporin derivative of formula (X), (ii) removing the acetyl group on the N-atom in the 7-aminocephalosporin derivative of formula (X) using PCl$_5$/POCl$_3$/pyridine, PCl$_5$/pyridine or triphenyl phosphite/Cl$_2$ complexes in the presence of an alcohol, at a temperature in the range of −40° C. to 0° C. to produce the compound of formula (IV), and (iii) isolating the compound of formula (IV).

The process is shown in Scheme-3 below

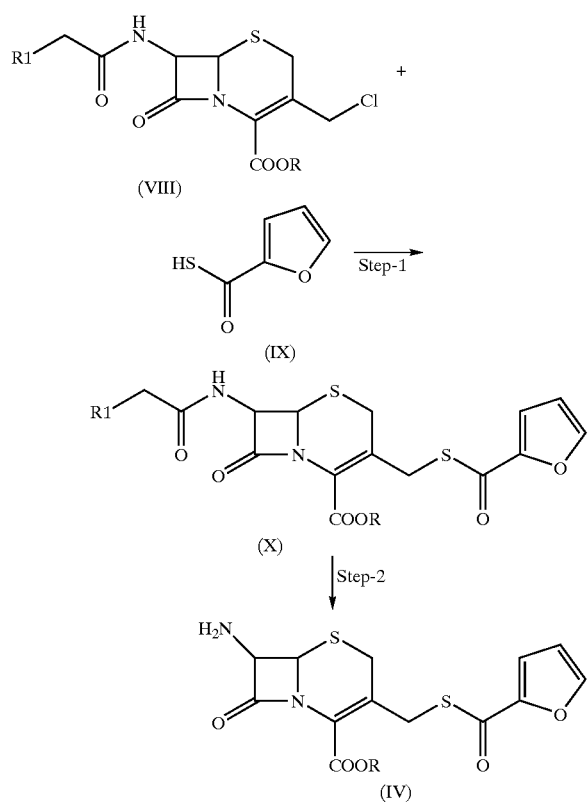

In yet another embodiment of the present invention, a the condensation in step (i) is performed by using the activated compound of formula (III) in the presence of a solvent selected from dichloromethane, ethyl acetate, tetrahydrofuran, aromatic hydrocarbon, acetone, dioxane, acetonitrile, N,N-dimethylformamide, dialkylethers, water or mixtures thereof.

The compound of formula (III) is activated as acid halides, mixed anhydrides, active esters, and active amides. The acid halides are acid chlorides or acid bromides. The mixed anhydrides are anhydrides of the compounds of formula (III) with pivaloyl chloride, ethyl chloroformate, benzyl chloroformate.

In yet another embodiment of the present invention the cyclisation in step (ii) is carried out using a mixture of water and organic solvent selected from tetrahydrofuran, acetone, acetonitrile, N,N-dimethylformamide, N,N-dimethylacetamide, dioxane, (C$_1$–C$_3$) alcohol or mixtures thereof.

In still another embodiment of the present invention, the deesterification in step (iii) is carried out using anisole/trifluoroacetic acid, phenol/trifluoroacetic acid or formic acid in the absence or presence of dichloromethane as a solvent. In another embodiment of the present invention, the pharmaceutically acceptable salt is sodium or hydrochloride.

In another embodiment of the present invention, the solvent used in scheme-2 is selected from tetrahydrofuran, acetone, acetonitrile, N,N-dimethylformamide, N,N-dimethylacetamide, dioxane, (C$_1$–C$_3$)alcohol or mixtures thereof, in the presence of a base selected from sodium acetate, potassium carbonate, triethylamine, 1,4-diazabicyclo-[2,2,2]-octane (DABCO), 1,5-diazabicyclo[4,3,0]-non-5-ene (DBN), 1,8-diaza-bicyclo[5,4,0]-undec-7-ene (DBU), pyridine or sodium carbonate.

In another embodiment of the present invention, the solvent used in step (i) of scheme-3 is selected from tetrahydrofuran, acetone, acetonitrile, N,N-dimethylformamide, N,N-dimethylacetamide, dioxane, (C$_1$–C$_3$)alcohol or mixtures thereof, in the presence of a base selected from sodium acetate, potassium carbonate, triethylamine, 1,4-diazabicyclo-[2,2,2]-octane (DABCO), 1,5-diazabicyclo[4,3,0]-non-5-ene (DBN), 1,8-diaza-bicyclo[5,4,0]-undec-7-ene (DBU), pyridine or sodium carbonate.

The compound of formula (IX) used in step (i) of scheme-3 is freshly prepared from furoyl chloride and sodium sulphide in a mixture of water and solvent selected from ethyl acetate or dichloromethane.

The substituents on R$_1$ in Scheme-3 are selected from methyl, methoxy, nitro, and halogen atom.

The present invention is provided by the examples below, which are provided by way of illustration only and should not be considered to limit the scope of the invention.

EXAMPLE-1

Preparation of 7-phenylacetamido-3-[(fur-2-ylcarbonyl)thiomethyl]-3-cephem-4-carboxylic Acid p-methoxybenzylester Flask A Acetone was charged and cooled to 10° C., 7-phenylacetamido-3-chloromethyl-3-cephem-4-carboxylic acid p-methoxybenzylester (100 g) was added. Sodium iodide (34.0 g) was added to it and mixture was stirred for 1–2 hr while temperature of the reaction mixture was maintained between 10–15° C.

Flask B

Water (200 ml) was taken and cooled to 20° C. and sodium sulphide (35.0 g) was added at 20° C. 2-Furoyl chloride (29.4 g) was added slowly drop wise into aqueous solution of sodium sulphide at 20° C. in 30 minutes. The reaction mixture was stirred at 20° C. for 1 hour added. Ethyl acetate (300 ml) was added and pH adjusted to 2–3 using 1:1 HCl [~50–60 ml] slowly. The organic layer was separated and dried over MgSO$_4$ (10 g).

The solution from flask A was transferred to flask B slowly at 10° C. Sodium carbonate anhydrous (23.0 g) was added and mixture was stirred at 10° C. for 30 minutes. The reaction was monitored by HPLC. After completion of reaction, the inorganic salts were filtered. To the clear filtrate, excess of water (~1500 ml) was added and stirred at 10–15° C. The solid separated out was filtered, washed with water and IPE.

| | |
|---|---|
| Yield = | 110 g |
| Purity(By HPLC) = | 98% |

$^1$H NMR-(DMSO-d$_6$) δ: 3.6 (s, 2H, 2-CH$_2$S), 3.7 (s, 2H, PhCH$_2$), 3.8 (s, 3H, —OMe), 4.2 (dd, 2H, —CH$_2$), 5.1 (d, 1H, C$_6$_H), 5.2 (s, 2H, O—CH$_2$—CO), 5.7 (dd, 1H, C$_7$_H), 6.8 (d, 1H, H-4 furan), 7.2–7.4 (m, 4H, Ar), 7.3 (d, 1H, H-3 furan), 8.0 (d, 1H, H-5 furan), 9.1(d, 1H, —CONH).

EXAMPLE-2

Preparation of 7-amino-3-[(fur-2-ylcarbonyl)thiomethyl]-3-cephem-4-carboxylic Acid p-methoxy benzyl ester Flask-A Dichloromethane (60 ml) was charged and cooled to −20° C. Phosphorous penta chloride (7.2 g) was added followed by $POCl_3$ (1.3 g) and the suspension was stirred for 15 minutes. Pyridine (7.0 g) was charged slowly at −30 to 40° C. The solution of 7-phenylacetamido-3-[(fur-2-ylcarbonyl)thiomethyl]-3-cephem-4-carboxylic acid p-methoxy benzyl ester (10.0 g) in 40 ml of dichloromethane was slowly added to this mixture. The reaction mixture was stirred for 1.0 hour at −30° C.

Flask-B

In an another flask, methanol (200 ml) was taken and cooled to −40° C. and to this cooled methanol, solution from flask A was added in 1.0 hour by maintaining temperature at −10 to −15° C. Solution becomes dark brown in color. Temperature was brought up to 0–10° C. The reaction was monitored by HPLC for complete disappearance of starting material. After completion of reaction, dichloromethane and methanol were removed under reduced pressure. To the residue was added a mixture of water (70 ml) and ethyl acetate (70 ml). Organic layer was separated and washed with water (3×50 ml) and with brine solution (50 ml). The org. layer was dried with $Na_2SO_4$ and evaporated to yield the title compound.

| | |
|---|---|
| Yield: | 6.0 g |
| Purity: | 97% |

$^1$H NMR-(DMSO-$d_6$) δ: 3.6 (s, 2H, 2-CH$_2$S), 3.8 (s, 3H, —OMe—), 4.2 (d, 2H, 3-CH$_2$S), 5.1 (d, 1H, C$_6$_H), 5.2 (s, 2H, O—CH$_2$—CO), 5.7 (dd, 1H, C$_7$_H), 6.8 (d, 1H, H-4 furyl), 7.2–7.4 (m, 4H, Ar), 7.3 (d, 1H, H-3 furyl), 8.0 (d, 1H, H-5 furyl).

EXAMPLE-3

Preparation of 7-[(2-(syn)methoxyimino-3-oxo-4-chlorobutyrylamino]-3-[(fur-2-ylcarbonyl)thiomethyl]-3-cephem-4-carboxylic acid p-methoxy benzyl ester Flask-A Dichloromethane (75 ml) was charged at room temperature, followed by 7-amino-3-[(fur-2-ylcarbonyl)thiomethyl]-3-cephem-4-carboxylic acid p-methoxy benzyl ester (15.0 g) and N,O-bis-(trimethylsilyl)acetamide (BSA) (100 g) drop wise at room temperature. The mixture was stirred at room temperature for 1 hour to get clear solution.

Flask-B

4-Chloro-3-oxo-methoxyimino-butyric acid (6.4 g) was dissolved in dichloromethane (75 ml) at room temperature. The solution was cooled to −30° C., PCl$_5$ (7.4 g) was added portion wise at −30° C. and stirred at −30° C. for 30 minutes. The reaction mass in flask B at −30° C. was transferred into pre cooled silylated mixture in flask A. Mixture was stirred at −30° C. for 15–20 minutes and progress of the reaction was monitored by HPLC. After completion of reaction, water (75 ml) was added slowly at 10° C. Organic layer was separated and washed again with water. IPE (200 ml) was added into organic layer at 10–20° C. to precipitate out the product. The solid was stirred at 20° C., filtered, washed with excess of water and IPE.

| | |
|---|---|
| Yield = | 12.0 g |
| Purity = | 98% |

$^1$H NMR-(DMSO-$d_6$) δ: 3.6 (dd, 2H, 2-CH$_2$S), 3.7(s, 3H, NOMe), 3.8 (s, 3H, —OMe), 4.2 (dd, 2H, —CH$_2$S), 4.8 (s, 2H, ClCH$_2$), 5.1 (d, 1H, C$_6$_H), 5.2 (S, 2H, O—CH$_2$_CO), 5.7 (dd, 1H, C$_7$_H), 6.8 (d, 1H, H$_4$_furan), 7.2–7.4 (m, 4H, Ar), 7.4 (d, 1H, H$_5$_furan), 8.0 (d, 1H, H$_5$_furan), 9.1 (d, 1H, —CONH).

EXAMPLE-4

Preparation of 7-[(2-(syn)methoxyimino-3-oxo-4-bromobutyrylamino]-3-[(fur-2-ylcarbonyl)thiomethyl]-3-cephem-4-carboxylic Acid p-methoxybenzylester Flask-A Dichloromethane (75 ml) was charged at room temperature, followed by the addition of 7-amino-3-[(fur-2-ylcarbonyl)thiomethyl]-3-cephem-4-carboxylic acid p-methoxy benzyl ester (15.0 g) and N,O-bis-(trimethylsilyl)acetamide (BSA) (100 g) drop wise at room temperature. The mixture was stirred at room temperature for 1 hour to get clear solution.

Flask-B

4-Bromo-3-oxo-methoxyimino-butyric acid (9.3 g) was dissolved in dichloromethane (75 ml) at room temperature. The solution was cooled to −30° C. and PCl$_5$ (7.4 g) was added portion wise at −30° C. The mixture was stirred at −30° C. for 30 minutes. The reaction mass in flask B at −30° C. was transferred into pre cooled silylated mixture in flask A. The reaction mixture was stirred at −30° C. for 15–20 minutes and progress of the reaction was monitored by HPLC. After completion of reaction, water (75 ml) was added slowly at 10° C. Organic layer was separated and washed again with water. IPE (200 ml) was added into organic layer at 10–20° C. to precipitate out the product. The solid was stirred at 20° C., filtered, washed with excess of water and IPE.

| | |
|---|---|
| Yield = | 12.0 g |
| Purity = | 98% |

$^1$H NMR-(DMSO-$d_6$) δ: 3.6 (dd, 2H, 2-CH$_2$S), 3.7(s, 3H, NOMe), 3.8 (s, 3H, —OMe), 4.2 (dd, 2H, —CH$_2$S), 4.6 (s,2H, BrCH$_2$); 5.1 (d, 1H, C$_6$_H), 5.2 (S, 2H, O—CH$_2$—CO), 5.7 (dd, 1H, C$_7$_H), 6.8 (d, 1H, H$_4$_furan), 7.2–7.4 (m, 4H, Ar), 7.4 (d, 1H, H$_5$_furan), 8.0(d, 1H, H$_5$_furan), 9.1 (d, 1H, —CONH).

EXAMPLE-5

Preparation of 7-[2-(2-aminothiazol-4-yl)-2-methoxyiminoacetamido]-3-[(fur-2-ylcarbonyl)thiomethyl]-3-cephem-4-carboxylic acid p-methoxy benzyl ester Tetrahydrofuran (50 ml) and water (50 ml) was charged into the reaction flask and to this 7-[(2-(syn)methoxyimino-3-oxo-4-chlorobutyrylamino]-3-[(fur-2-ylcarbonyl)thiomethyl]-3-cephem-4-carboxylic acid p-methoxybenzylester (10.0 g) was added at room temperature. Thiourea (2.0 g) and sodium acetate (1.6 g) were added at room temperature. The reaction was monitored by HPLC and after completion of reaction, water (50 ml) and MDC (100 ml) were added to reaction mass. Organic layer was separated and washed with water (100 ml). Organic layer was added into IPE solvent (200 ml) at room temperature in 30 minutes, cooled to 10–20° C., filtered and washed with water (100 ml) and IPE (50 ml).

| | |
|---|---|
| Yield = | 7.0 g |
| Purity = | 96% |

¹H NMR-(DMSO-d₆) δ: 3.6 (dd, 2H, 2-CH₂S), 3.7 (s, 3H, —OMe), 3.8 (s, 3H, —OMe), 4.2 (dd, 2H, —CH₂S), 5.1 (d, 1H, C₆-H), 5.2 (m, 2H, O—CH₂—CO), 5.7 (dd, 1H, C₇-H), 6.7 (s, 1H, H-thiazole), 6.8 (m, 1H, H₄-furyl), 7.15 (s, 2H, —NH₂ thiazole), 7.2–7.4 (m, 4H, Ar), 7.4 (d, 1H, H₃-furyl), 8.0 (d, 1H, H₅-furan), 9.1 (d, 1H, —NH).

EXAMPLE-6

Preparation of Ceftiofur Sodium

Dichloromethane (20 ml) was charged and cooled to 0–5° C., 7-[2-(2-aminothiazol-4-yl)-2-methoxyiminoacetamido]-3-[(fur-2-ylcarbonyl)thiomethyl]-3-cephem-4-carboxylic acid p-methoxy benzyl ester (6.5 g) was added followed by trifluoroacetic acid (20 ml) at 0–5° C. The reaction mixture was stirred for 30–40 min. Anisole (12 ml) was also added at 5° C. and reaction was stirred at 5° C. for 1 hour, the reaction was checked by HPLC and after completion of reaction, water (100 ml) was added with stirring. The product was filtered and washed with water (100 ml) followed by dichloromethane (100 ml). The filtered solid was taken in tetrahydrofuran (100 ml) and dried over MgSO₄. To the dried THF layer was added a solution of 5 g of 2-ethyl sodium hexanoate in THF (20 ml). The precipitated ceftiofur sodium was stirred for 30 minutes at 20° C. filtered and washed with acetone (100 ml).

| | |
|---|---|
| Yield = | 5.0 g |
| Purity = | 99% |

What is claimed is:

1. A process for the preparation of Ceftiofur acid of formula (I):

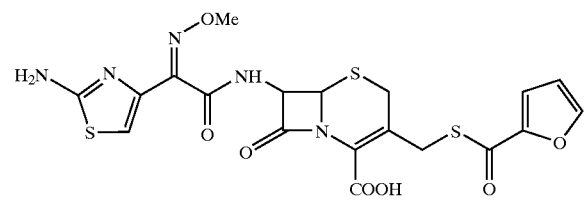

(I)

and its pharmaceutically acceptable salts selected from sodium and hydrochloride salts, wherein Me represents methyl, the process comprising the steps of:

(I) condensing an activated derivative of a compound of formula (III):

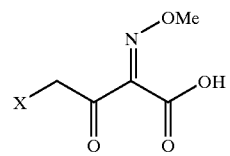

(III)

wherein the activated derivative of the compound of formula (III) is selected from an acid halide, a mixed anhydride and an active amide, wherein Me represents methyl, and wherein X represents halogen atom selected from chlorine and bromine, with silylated derivative of 7-amino cephalosporin of formula (IV):

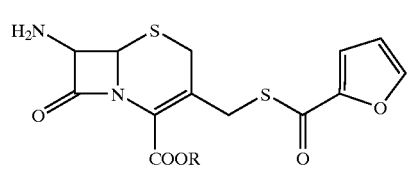

(IV)

wherein R represents p-methoxybenzyl, p-nitrobenzyl or diphenylmethyl group, in the presence of a solvent at a temperature in the range of −40° C. to 0° C. to produce a compound of formula (V):

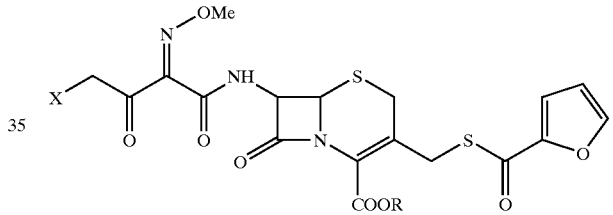

(V)

wherein R is as defined earlier, (ii) cyclising the compound of formula (V) with thiourea in the presence of water miscible solvent and sodium acetate at room temperature to produce cephalosporin compounds of formula (VI);

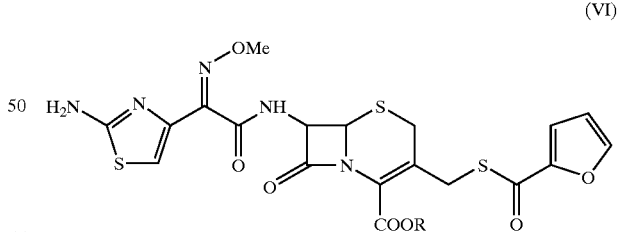

(VI)

wherein R and Me is as defined earlier, (iii) deesterifying the compound of formula (VI) to produce the compound of formula (I) using anisole/trifluoroacetic acid, phenol/trifluoroacetic acid or formic acid in the presence or absence of a solvent at a temperature in the range of 0° C. to 10° C. and, if desired, (iv) converting the compound of formula (I), to its pharmaceutically acceptable salt.

2. The process of claim 1, wherein said compound of formula (I) is a syn isomer.

3. The process of claim 1, wherein the condensation in step (i) is performed by using the activated compound of formula (III) in the presence of a solvent selected from dichloromethane, ethyl acetate, tetrahydrofuran, aromatic hydrocarbon, acetone, dioxane, acetonitrile, N,N-dimethylformamide, dialkylethers or mixtures thereof.

4. An intermediate of formula (V):

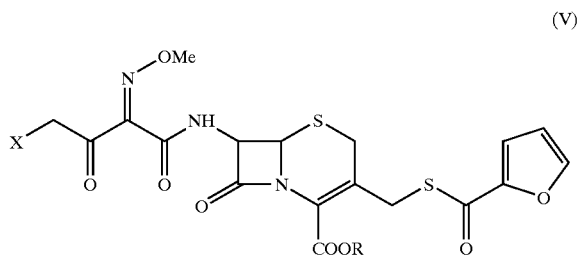

(V)

wherein X represents halogen atom selected from chlorine and bromine, wherein Me represents methyl, and wherein R represents p-methoxybenzyl, p-nitrobenzyl or diphenylmethyl group.

5. The process of claim 1, wherein the activated derivative is an acid halide selected from acid chlorides and acid bromides.

6. The process of claim 1, wherein the activated derivative is a mixed anhydride selected from anhydrides of the compounds of formula (III) with pivaloyl chloride, ethyl chloroformate, or benzyl chloro formate.

7. The process of claim 1, wherein the cyclisation in step (ii) is carried out using a mixture of water and organic solvent selected from tetrahydrofuran, acetone, acetonitrile, N,N-dimethylformamide, N,N-dimethylacetamide, dioxane, ($C_1$–$C_3$) alcohol or mixtures thereof.

8. An intermediate of formula (VI):

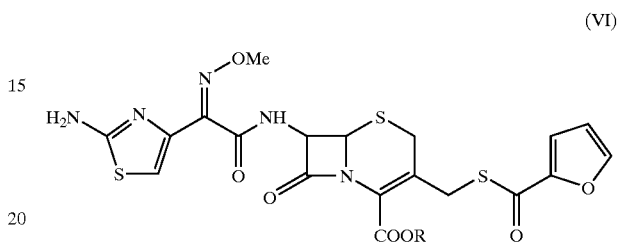

(VI)

wherein Me represents methyl, and wherein R represents p-methoxybenzyl, p-nitrobenzyl or diphenylmethyl group.

* * * * *